US00PP29685P2

(12) United States Plant Patent
Bernuetz

(10) Patent No.: US PP29,685 P2
(45) Date of Patent: Sep. 18, 2018

(54) ***EUPHORBIA* PLANT NAMED 'BONPOIAKANI'**

(50) Latin Name: ***Euphorbia pulcherrima* Willd. ex Klotzsch**
Varietal Denomination: Bonpoiakani

(71) Applicant: Andrew Bernuetz, Silverdale (AU)

(72) Inventor: Andrew Bernuetz, Silverdale (AU)

(73) Assignee: Bonza Botanicals Pty., Ltd., Yellow Rock, NSW (AU)

( * ) Notice: Subject to any disclaimer, the term of this patent is extended or adjusted under 35 U.S.C. 154(b) by 0 days.

(21) Appl. No.: 15/530,826

(22) Filed: Mar. 3, 2017

(51) Int. Cl.
*A01H 5/02* (2018.01)

(52) U.S. Cl.
USPC ..... Plt./307

(58) Field of Classification Search
USPC ..... Plt./307
See application file for complete search history.

*Primary Examiner* — Anne Marie Grunberg
(74) *Attorney, Agent, or Firm* — C. A. Whealy

(57) ABSTRACT

A new and distinct cultivar of *Euphorbia* plant named 'Bonpoiakani', characterized by its upright and mounded plant habit; moderately vigorous growth habit; freely branching habit; inflorescences with large intense red-colored flower bracts that resist damage during transportation; relative low temperature tolerance during production; and good post-production longevity.

1 Drawing Sheet

Botanical designation: *Euphorbia pulcherrima* Willd. ex Klotzsch.

Cultivar denomination: 'BONPOIAKANI'.

BACKGROUND OF THE INVENTION

The present invention relates to a new and distinct cultivar of *Euphorbia* plant, botanically known as *Euphorbia pulcherrima* Willd. ex Klotzsch, and hereinafter referred to by the cultivar name 'Bonpoiakani'.

The new *Euphorbia* plant is a product of a planned breeding program conducted by the Inventor in Yellow Rock, New South Wales, Australia. The objective of the program is to create and develop new interspecific *Euphorbia* plants with upright and mounded plant habit and large sturdy flower bracts and relative tolerance to low temperatures.

The new *Euphorbia* plant originated from a cross-pollination by the Inventor in May, 2008 of a proprietary selection of *Euphorbia pulcherrima* Willd. ex Klotzsch identified as code number 524, not patented, as the female, or seed, parent with a proprietary selection of *Euphorbia pulcherrima* Willd. ex Klotzsch identified as code number 397, not patented, as the male, or pollen, parent. The new *Euphorbia* plant was discovered and selected by the Inventor as a single flowering plant within the progeny of the stated cross-pollination in a controlled greenhouse environment in Yellow Rock, New South Wales, Australia on Nov. 10, 2009.

Asexual reproduction of the new *Euphorbia* plant by terminal vegetative cuttings in a controlled greenhouse environment in Yellow Rock, New South Wales, Australia since November, 2009 has shown that the unique features of this new *Euphorbia* plant are stable and reproduced true to type in successive generations of asexual reproduction.

SUMMARY OF THE INVENTION

Plants of the new *Euphorbia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Bonpoiakani'. These characteristics in combination distinguish 'Bonpoiakani' as a new and distinct *Euphorbia* plant:

1. Upright and mounded plant habit.
2. Moderately vigorous growth habit.
3. Freely branching habit.
4. Inflorescences with large intense red-colored flower bracts that resist damage during transportation.
5. Relative low temperature tolerance during production.
6. Good post-production longevity.

In side-by-side comparisons, plants of the new *Euphorbia* differ primarily from plants of the female parent selection in the following characteristics:

1. Plants of the new *Euphorbia* are larger than and not as compact as plants of the female parent selection.
2. Plants of the new *Euphorbia* and the female parent selection differ in flower bract shape as plants of the female parent selection have flower bracts with serrated margins.

In side-by-side comparisons, plants of the new *Euphorbia* differ primarily from plants of the male parent selection in the following characteristics:

1. Plants of the new *Euphorbia* have larger flower bracts than plants of the male parent selection.
2. Flower bracts of plants of the new *Euphorbia* have shorter petioles than flower bracts of plants of the male parent selection.

Plants of the new *Euphorbia* can be compared to plants of the *Euphorbia pulcherrima* Willd. 'Eckadire', disclosed in U.S. Plant Pat. No. 12,846. In side-by-side comparisons, plants of the new *Euphorbia* differ primarily from plants of 'Eckadire' in the following characteristics:

1. During production, plants of the new *Euphorbia* are more low temperature tolerant than plants of 'Eckadire'.
2. Plants of the new *Euphorbia* flower about one week earlier than plants of 'Eckadire'.
3. Plants of the new *Euphorbia* and 'Eckadire' differ in flower bract color as plants of 'Eckadire' have darker red-colored flower bracts.
4. During transportation, flower bracts of plants of the new *Euphorbia* are more resistant to damage than flower bracts of plants of 'Eckadire'.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph at the top of the sheet is a side perspective view of a typical flowering plant of 'Bonpoiakani' grown in a container.

The photograph at the bottom of the sheet is a close-up view of a typical flowering plant of 'Bonpoiakani'.

DETAILED BOTANICAL DESCRIPTION

Plants used in the aforementioned photographs and described herewith in detail were grown during the autumn in 12-cm containers in an outdoor nursery in Higashiomi, Shiga, Japan and under cultural practices typical of commercial *Euphorbia* production. During the production of the plants, day temperatures averaged 23° C. and night temperatures averaged 13° C. Plants were five months old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. ex Klotzsch 'Bonpoiakani'.

Parentage:

*Female, or seed, parent*.—Proprietary selection of *Euphorbia pulcherrima* Willd. ex Klotzsch identified as code number 524, not patented.

*Male, or pollen, parent*.—Proprietary selection of *Euphorbia pulcherrima* Willd. ex Klotzsch identified as code number 397, not patented.

Propagation:

*Type*.—Terminal vegetative cuttings.

*Time to initiate roots, summer*.—About seven days at temperatures about 20° C. to 25° C.

*Time to initiate roots, winter*.—About nine days at temperatures about 20° C. to 22° C.

*Time to produce a rooted young plant, summer*.—About three weeks at temperatures about 20° C. to 25° C.

*Time to produce a rooted young plant, winter*.—About four weeks at temperatures about 20° C. to 22° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant habit and form*.—Upright and mounded plant habit; inverted triangle; inflorescences positioned above the foliar plane; moderately vigorous growth habit.

*Plant height*.—About 17 cm.

*Plant diameter or spread*.—About 30 cm.

*Lateral branch description*.—Branching habit: Freely branching habit, about four lateral branches develop per plant; pinching is not required. Length: About 9.4 cm. Diameter: About 4.2 mm. Internode length: About 1.6 cm. Aspect: Mostly upright to somewhat outwardly. Strength: Strong. Texture and luster: Smooth, glabrous; glossy. Color: Close to 146B.

*Leaf description*.—Arrangement: Alternate, simple. Length: About 7.5 cm. Width: About 4.2 cm. Shape: Ovate. Apex: Acute. Base: Cuneate. Margin: Shallowly serrate, irregular. Texture and luster, upper surface: Sparsely pubescent; matte. Texture and luster, lower surface: Sparsely pubescent; prominent venation; matte. Venation pattern: Pinnate, reticulate. Color: Developing leaves, upper surface: Close to 137A. Developing leaves, lower surface: Close to 138B. Fully developed leaves, upper surface: Close to N137D; venation, close to 173D. Fully developed leaves, lower surface: Close to 147B; venation, close to 173D and 145C. Petioles: Length: About 2.4 cm. Diameter: About 1.7 mm. Texture, upper and lower surfaces: Smooth, glabrous. Color, upper surface: Close to 182A. Color, lower surface: Close to 183B.

Inflorescence description:

*Inflorescence type and habit*.—Inflorescences are compound corymbs of cyathia with numerous flower bracts subtending the cyathia; inflorescences positioned above the foliar plane; during transportation, flower bracts resist damage.

*Quantity of inflorescences*.—About four inflorescences develop per plant.

*Inflorescence diameter*.—About 22.3 cm.

*Inflorescence height*.—About 5.1 cm.

*Fragrance*.—None detected.

*Natural flowering season*.—Plants typically flower during the autumn and winter in Japan; inflorescence initiation and development can also be induced under artificial long nyctoperiod and short photoperiod conditions; early flowering habit, plants flower about seven weeks under natural season conditions in Japan.

*Post-production longevity*.—Good post-production longevity; plants of the new *Euphorbia* maintain good substance and bract color for about seven weeks.

*Flower bracts*.—Quantity per inflorescence: About eight. Length, largest bracts: About 8 cm. Width, largest bracts: About 4 cm. Shape: Ovate. Apex: Cuspidate. Base: Cuneate. Margin: Entire; very slightly undulate. Texture and luster, upper and lower surfaces: Smooth, glabrous; matte. Aspect: Slightly upright to horizontal. Venation pattern: Pinnate, reticulate. Color: Transitional bracts, upper surface: Random sectors, close to 144C, 143C, 53C and 50B. Transitional bracts, lower surface: Random sectors, close to N170D and 185D; apex, close to 145A. Developing bracts, upper surface: Close to 45B.

Developing bracts, lower surface: Close to 47B. Fully expanded bracts, upper surface: Close to 46B; venation, close to 183B. Fully expanded bracts, lower surface: Close to 47B; venation, close to 181B. Flower bract petioles: Length: About 1.6 cm. Diameter: About 1.5 mm. Texture, upper and lower surfaces: Smooth, glabrous. Color, upper surface: Close to 183C. Color, lower surface: Close to 47A.

*Cyathia*.—Quantity per corymb: About seven. Diameter of cyathia cluster: About 1.9 cm. Height, individual cyathium: About 5.4 mm. Diameter, individual cyathium: About 6.7 mm. Shape, individual cyathium: Globose. Color: Close to 143B; towards the apex, close to 53B. Nectaries: Quantity per cyathium: One or two. Height, individual nectary: About 2.5 mm. Diameter, individual nectary: About 4.7 mm. Color: Close to 7A.

*Peduncles*.—Length: About 2.8 mm. Diameter: About 1.8 mm. Strength: Strong. Aspect: Upright. Texture: Smooth, glabrous. Color: Close to 145A.

*Reproductive organs*.—Stamens: Quantity per cyathium: About five. Filament length: About 5.7 mm. Filament color: Close to 59A. Anther size: About 0.8 mm by 0.5 mm. Anther shape: Lanceolate or globose. Anther color: Close to 163A and 179A. Amount of pollen: Sparse. Pollen color: Close to 5A. Pistils: To date, plants of the new *Euphorbia* have not been observed to develop pistils. Seeds and fruits: To date, seed and fruit production has not been observed on plants of the new *Euphorbia*.

Disease & pest resistance: Plants of the new *Euphorbia* have not been shown to be resistant to pathogens and pests common to *Euphorbia* plants.

Temperature tolerance: Plants of the new *Euphorbia* have been observed to tolerate temperatures ranging from about 8° C. to about 40° C.

It is claimed:

1. A new and distinct *Euphorbia* plant named 'Bonpoiakani' as illustrated and described.

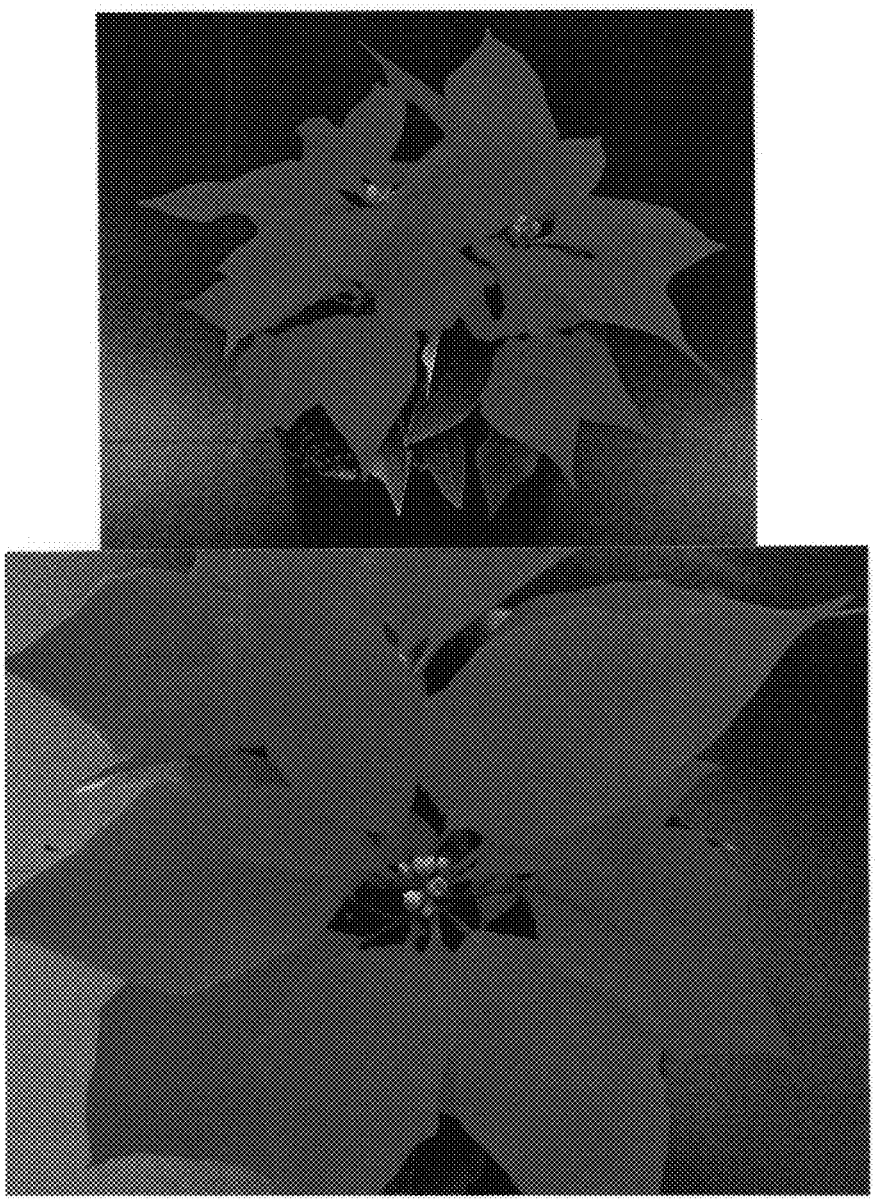

* * * * *